United States Patent
Erickson et al.

(10) Patent No.: US 7,937,158 B2
(45) Date of Patent: May 3, 2011

(54) MULTI-PROGRAMMABLE TRIAL STIMULATOR

(75) Inventors: John H Erickson, Plano, TX (US); George Van Campen, Fort Lauderdale, FL (US); Patrick M Cullen, Dallas, TX (US); Thomas K Hickman, Plano, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 201 days.

(21) Appl. No.: 12/243,632

(22) Filed: Oct. 1, 2008

(65) Prior Publication Data

US 2009/0024187 A1   Jan. 22, 2009

Related U.S. Application Data

(63) Continuation of application No. 11/122,540, filed on May 5, 2005, now abandoned.

(60) Provisional application No. 60/568,384, filed on May 5, 2004.

(51) Int. Cl.
*A61N 1/08*   (2006.01)
(52) U.S. Cl. .......................................... 607/59; 607/13
(58) Field of Classification Search ................ 607/2, 59, 607/646, 64, 13
See application file for complete search history.

(56) References Cited

U.S. PATENT DOCUMENTS

| | | | |
|---|---|---|---|
| 3,942,535 A | 3/1976 | Schulman | |
| 5,486,201 A | 1/1996 | Canfield | |
| 5,693,076 A | 12/1997 | Kaemmerer | |
| 5,948,004 A | 9/1999 | Weijand et al. | |
| 6,381,496 B1 | 4/2002 | Meadows et al. | |
| 6,516,227 B1 | 2/2003 | Meadows et al. | |
| 6,895,278 B1 * | 5/2005 | Gordon | 607/40 |
| 7,181,505 B2 | 2/2007 | Haller et al. | |
| 7,359,751 B1 | 4/2008 | Erickson et al. | |

* cited by examiner

*Primary Examiner* — Eric D. Bertram
(74) *Attorney, Agent, or Firm* — Christopher S. L. Crawford; Peter Lando; Craig Hoersten

(57) ABSTRACT

Disclosed are systems and methods which provide trial stimulators suited for use interoperatively and during patient trial. Trial stimulator embodiments provide a patient interface and/or clinician interface which appears and functions substantially the same as an interface of a pulse generator controller which will be used after a trial period. A compliance monitor feature may be provided to facilitate verifying the proper use of the trial stimulator during a trial period. A diagnostic feature may be provided to facilitate verifying proper operation of various aspects of a trial stimulator, such as electrode impedance analysis. Trial stimulators of embodiments provide stimulation to a plurality of tissues and/or areas of the body, such as spinal cord stimulation, deep brain stimulation, etcetera. Embodiments provide for multi-electrode stimulation and multi-stimulation programs. Embodiments are configured to provide active discharge of stimulation pulses as well as to utilize constant current sources in providing the stimulation pulses.

7 Claims, 3 Drawing Sheets

MULTI-PROGRAMMABLE TRIAL STIMULATOR

CROSS-REFERENCE TO RELATED APPLICATIONS

This application is a continuation of prior U.S. application Ser. No. 11/122,540, filed May 5, 2005, which claims the benefit of U.S. Provisional Application No. 60/568,384, filed May 5, 2004 and is related to commonly assigned U.S. application Ser. No. 11/122,706, filed May 5, 2005, now U.S. Pat. No. 7,359,751, the disclosures of which are fully incorporated herein by reference.

TECHNICAL FIELD

The present invention relates generally to electronic tissue stimulators and, more particularly, to electronic tissue stimulators adapted for use in stimulation trial situations.

BACKGROUND OF THE INVENTION

The use of electronic stimulation systems to control pain by nerve or muscle stimulation has been in use for a number of years. For example, spinal cord stimulation (SCS) is a technique that has been used for pain management since the 1960s. SCS systems generally feature a pulse generator coupled to one or more percutaneous leads having a plurality of electrodes disposed in an area in which neurostimulation is desired.

The pulse generator may be provided in various configurations, such as a totally implanted pulse generator (IPG) or a radio frequency (RF) system. A typical IPG configuration comprises a surgically implanted, internally-powered pulse generator and multi-electrode lead. A typical RF system configuration comprises a surgically implanted, passive receiver and a transmitter which is worn externally. In operation, the transmitter communicates, through an RF signal, to the implanted receiver to provide stimulation energy and control.

The leads used with any of the foregoing pulse generators may be positioned within a patient's epidural space, typically parallel to the axis of the spinal cord. The electrodes are used to deliver a particularized electric field to a specific region of the spinal cord or surrounding tissue. Applying an electric field across one or more nerve bundles and/or nerve roots can produce paresthesia, or a subjective sensation of numbness, tingling or "pins and needles," at the affected nerves' dermatomes. This paresthesia, if properly directed and produced at the necessary levels, can "mask" certain forms of chronic pain.

Implantation of a pulse generator, whether a fully implanted IPG or a RF system receiver/transmitter, necessarily requires a neurostimulation patient to undergo an implantation surgery. Additionally, routing a lead subdermally between an implanted pulse generator and the tissue area to be stimulated typically requires a relatively invasive procedure, such as a tunneling procedure. However, a lead having electrodes thereon suitable for providing neurostimulation when coupled to a pulse generator may be implanted through much less invasive means, such as through a laparoscopic needle procedure.

The focus, characteristics and intensity of the generated electric field are determined by the electrode configuration (i.e., the polarity, if any, assumed by each electrode) and the electric pulse waveform (collectively "stimulation setting"). The waveform properties include, at least, a stimulation frequency, a stimulation pulse width and phase information.

Accordingly, a physician, nurse, or clinician (referred to collectively herein as clinician) may advantageously couple a pulse generator to a lead or leads in the course of performing a lead and/or generator implantation procedure on a patient in order to confirm proper operation of neurostimulation. For example, a clinician may couple a pulse generator to a lead during a lead implantation procedure to confirm the electrodes are disposed at a proper location within the patient. Similarly, prior to implantation of a pulse generator, a clinician may couple a pulse generator to a lead to determine the stimulation setting to implement in the implanted pulse generator in order to achieve the desired results.

Additionally or alternatively, a patient may wish to experience neurostimulation for a period of time, before undergoing procedures for implanting a pulse generator and subdermally coupling a lead thereto, in order to determine if the feeling associated with paresthesia is acceptable to the patient and that the therapy acceptably masks the patient's pain. Accordingly, a lead or leads (perhaps "trial" leads to be removed and subsequently replaced with "permanent" leads upon successful conclusion of a trial period) may be laparoscopically or surgically inserted, with an end distal to the electrodes left external for coupling to a pulse generator. With a suitable pulse generator coupled to the lead, the patient may experience the prescribed neurostimulation therapy for a trial period, e.g., several hours to 30 days, to determine if the therapy is satisfactory before undergoing implantation procedures.

Various forms of pulse generators have been provided in configurations adapted for the foregoing trial uses (such pulse generators being referred to herein as "trial stimulators"). These trial stimulators have typically been relatively limited in their functionality and features. For example, trial stimulators available today provide for connection to either 4, 8, or 16 electrodes and no more.

Generally, the same trial stimulator configuration is used whether the patient or the clinician is conducting the trial, although a patient may be restricted from accessing certain features of the trial stimulator. For example, a micro-switch bank may be provided to allow a clinician to select stimulation pulse widths and amplitudes, with a cover being provided to prevent a patient from accessing the micro-switch bank during their trial period. Additionally or alternatively, a lock-out switch or mechanism may be implemented to prevent a patient having physical access to particular control means, such as the aforementioned micro-switch bank, from altering particular operational aspects of the trail stimulator.

The foregoing trial stimulators do not present an interface which is equally easy to use in the various situations they are expected to be used in, e.g., interoperatively in the operating room and patient trial. For example, where features or functions are provided for ready access when used interoperatively, such as to provide complex control alternatives for establishing a precisely tailored stimulation program, the trial stimulator is typically not well suited for use by the patient. Likewise, where relatively simple and intuitive features or functions are provided for simplified access during a patient trial, such as to facilitate a patient manipulating a relatively complex stimulation program to experience various stimulation parameters in a home trial, the trial stimulator is typically not well suited for use by the clinician.

Trial stimulators that have been provided in the past have generally delivered constant voltage pulses to the lead electrodes. Traditional wisdom has been that by delivering constant voltage, if an electrode should fail (e.g., become disconnected from the stimulator) the voltage to the system would remain unchanged, thus having no change on battery life and presenting little risk of over stimulation because the voltage to the remaining electrodes would remain substantially unchanged.

Although providing some form of real-time variable stimulation, the trial stimulators available today do not provide true continuous multi-stimulation programs. By multi-stimulation programs, it is meant that a first set of stimulation parameters (e.g., amplitude, pulse width, frequency, and electrodes) are implemented to provide a first desired therapy (e.g., relieve pain associated with a first portion of the body) and a second set of stimulation parameters are implemented to provide a second therapy (e.g., relieve pain associated with a second portion of the body). Multi-stimulation programs of prior trial stimulators have implemented each stimulation parameter set for a predetermined period of time (multiple stimulation pulses) before moving to a next stimulation parameter set. Even where a few different stimulation program sets are used, e.g., 3, the cycle time for the trial stimulator returning to the first stimulation program set may be high. Patients have stated that such a periodic cycling of stimulator parameter sets sometimes results the patient being able to feel the stimulation cycles as a "fluttering" which, although not particularly unpleasant, is noticeable.

Another attempt at providing a patient with multiple stimulation programs using a trial stimulator has been to implement dual stimulation. For example, a trial stimulator having 8 channels may be provide a first stimulation parameter set to 4 electrodes while providing a second stimulation program parameter set to a different 4 electrodes.

BRIEF SUMMARY OF THE INVENTION

The present invention is directed to systems and methods which provide stimulators well suited for use in a plurality of situations, such as interoperatively and during patient trial (e.g., trial stimulators). Additionally, trial stimulators of the present invention are adapted to provide robust functionality, preferably with respect to their programming as well as their operation.

Preferred embodiments of the present invention provide a trial stimulator having a user interface which is well suited for patient trial use. For example, a trial stimulator configured according to embodiments of the present invention preferably provides an intuitive interface having graphical, textual, and/or aural prompting and simple user input. According to one embodiment, graphical displays such as may include a battery life indicator, stimulation pulse amplitude and/or frequency, etcetera is provided to aid a user in readily interpreting the status of various aspects of a trial stimulator. Trial stimulator embodiments preferably provide a patient interface which appears and functions substantially the same as a user interface of a pulse generator controller which will be used for controlling a pulse generator (implanted or otherwise) after the trial period, thereby allowing a patient to learn a single interface.

Embodiments of the present invention additionally or alternatively provide a trial stimulator having a user interface which is well suited for clinician use. For example, a trial stimulator user interface configured according to embodiments of the present invention may facilitate simplified use between a plurality of patients by automatically resetting stimulation parameter sets and/or other parameters to an initialization state (or perhaps querying a clinician in this regard) when a clinician mode is entered.

A compliance monitor feature is preferably provided by a clinician interface of embodiments of the invention to facilitate a clinician verifying the proper use of the trial stimulator during a trial period. For example, a compliance monitor may record information with respect to the operation of a trial stimulator, including stimulation parameters, programs implemented, time and duration of operation of stimulation sets, etcetera, in order to allow a clinician to subsequently determine if a patient has used the trial stimulator according to a prescribed therapy, to diagnose a patient's reported indications, etcetera.

A diagnostic feature is preferably provided by a clinician interface of embodiments of the invention to facilitate a clinician verifying proper operation of various aspects of a trial stimulator. For example, diagnostic algorithms may be implemented which check system integrity. According to preferred embodiments, diagnostic algorithms provide for electrode impedance analysis, such as for testing electrodes, determining if electrodes should be replaced when a stimulation generator is being replaced, determining if open or short circuits are present, etcetera. For example, a diagnostic algorithm of one embodiment may step a test signal through combinations of electrodes to determine if an acceptable impedance is present with respect to each bipole pair, possibly providing a graphical display to readily show if impedances are acceptable or not. Impedance determinations according to the foregoing may utilize constant current circuitry described below in providing a sampling signal (e.g., a square wave) to electrodes for measuring impedance.

Full clinician user interface functionality, such as may include initialization, programming, monitoring, status reporting, etcetera, is preferably included within a trial stimulator of the present invention. For example, a clinician interface incorporated within a trial stimulator of an embodiment may provide an interface which appears and functions substantially the same as a clinician interface of a pulse generator controller which will be used for controlling a pulse generator (implanted or otherwise) after the trial period, thereby allowing a clinician to learn a single interface.

In order to facilitate the aforementioned intuitive patient interface and full featured and intuitive clinician interface without presenting a number of inputs and/or outputs which, although present in a patient trial mode, are not used by a patient, embodiments of the present invention implement an external clinician interface, preferably in addition to the aforementioned internal clinician interface. For example, according to embodiments of the present invention, an external platform having appreciable input/output capability, such as a laptop computer or a personal digital assistant (PDA), is adapted to cooperate with a trial stimulator to provide a clinician interface according to the present invention. Accordingly, although a clinician may be enabled to access all features and functions through manipulation of an interface integral with the trial stimulator, a more robust interface, perhaps using enhanced graphics, color, sound, speech recognition, etcetera, may be provided to a clinician using the aforementioned external platform.

The aforementioned external clinician interface platforms may be coupled to a trial stimulator of the present invention using wired (e.g., universal serial bus (USB), Ethernet, fiber optic, etcetera) links and/or wireless links (e.g., infrared, bluetooth, Institute of Electrical and Electronic Engineers (IEEE) 802.11 wireless communication, etcetera). Accordingly, preferred embodiments of the present invention provide a clinician interface which may easily be disposed at various locations convenient to the clinician, even locations beyond the sterile field of an operating room.

Trial stimulators of embodiments of the present invention are adapted for use in providing stimulation to a plurality of tissues and/or areas of the body, such as spinal cord stimulation, deep brain stimulation, etcetera. Accordingly, a user interface provided according to embodiments of the present invention provides multi-mode patient and/or clinician interfaces adapted to present an interface specific to a particular use. For example, although perhaps sharing a number of features and functions, separate patient and/or clinician interfaces for spinal cord stimulation and deep brain stimulation may be provided with respect to a trial stimulator. Utilization of a particular mode may provide for different trial stimulator operating characteristics, such as to implement smaller or larger amplitude increments when adjusting a stimulation pulse amplitude parameter in the various modes of operation.

Embodiments of the present invention provide multi-channel trial stimulators. For example, an embodiment of the present invention provides 32 separate channels allowing control of 32 electrodes in any of three states (positive polarity, negative polarity, and neutral). According to embodiments, the plurality of channels may be coupled to one or more leads, each having one or more electrodes. For example, a single lead having 32 electrodes may be controlled by a trial stimulator of embodiments of the present invention. Likewise, 2 leads having 8 electrodes each and 1 lead having 16 electrodes may be controlled by a trial stimulator of embodiments of the present invention, such as to provide neurostimulation of different parts of a patient's body. Of course, all channels provided by a trial stimulator need not be coupled to a corresponding electrode, if desired. Moreover, embodiments of the present invention provide for simultaneously controlling leads placed in different tissue types, such as to stimulate spinal regions and brain areas, using a single trial stimulator.

A trial stimulator configuration of an embodiment of the present invention provides a lead cable extension for coupling the trial stimulator to one or more of the foregoing leads. For example, a midline connector may be provided with respect to a trial lead cable configuration to allow the trial stimulator to be disposed at various locations convenient to the clinician, even locations beyond the sterile field of an operating room, while allowing a relatively short lead cable to be used during patient trial. In use, the midline connector may be decoupled after interoperative use of a trial stimulator by a clinician to facilitate removal of a lead extension from the trial stimulator and connection of the trial stimulator to the trial lead, thereby avoiding excess lengths of lead cable during subsequent patient trial.

In energizing the aforementioned plurality of electrodes, embodiments of the present invention provide multiple stimulation programs. For example, a first stimulation program may be implemented with respect to a particular time of day or when a patient is involved in a particular activity, whereas a second stimulation program may be implemented with respect to a different time of day or when the patient is involved in another activity. According to a preferred embodiment, 24 different stimulation programs may be stored in a trial stimulator, such as for selection by a user and/or automated implementation by the trial stimulator control algorithms.

According to embodiments of the invention, stimulation programs may implement multiple stimulation parameter sets (a set of stimulation parameters such as may specify amplitude, pulse width, frequency, and electrodes), thereby providing multi-stimulation programs. The stimulation parameter sets implemented by a stimulation program of a preferred embodiment trial stimulator are changeable dynamically during operation of the stimulation program (e.g., "on the fly"). For example, stimulation parameters such as amplitude, pulse width, frequency, polarity, and/or selection of electrodes may be changed as a stimulation program continues to operate to provide stimulation. Accordingly, selecting appropriate stimulation settings, even where multiple stimulation parameter sets are employed, is streamlined according to embodiments of the invention. Moreover, interaction between multiple stimulation parameter sets may be detected and compensated for more easily using dynamic stimulation parameter adjustment provided according to preferred embodiments. For example, a clinician may implement a first stimulation parameter set, leave that stimulation set running, and then bring in another stimulation parameter set along side of it and see if the combination of stimulation parameter sets (e.g., multi-stimulation program) is better for the patient actively, rather than testing each individually and then trying to join them together to ask the patient how the combination feels. Accordingly, a clinician may adjust stimulation parameter sets dynamically and interactively with the patient to change and optimize the stimulation therapy.

In operation according to preferred embodiments, the multiple stimulation parameter sets of a multi-stimulation program are implemented in an interleaved fashion (e.g., a first stimulation parameter set is energized for a single pulse, followed by a second stimulation parameter set being energized for a single pulse) rather than energizing each stimulation parameter set for a predetermined period of time (e.g., multiple stimulation pulses) before moving to a next stimulation parameter set. Of course, stimulation programs of embodiments of the present invention may energize one or more stimulation parameter set of a multi-stimulation program for a predetermined period of time, where desired.

To facilitate operation of multi-stimulation programs, such as those implemented in an interleaved or pulse-by-pulse fashion as described above, embodiments of the invention are configured to provide active discharge of electrode energizing pulses. Specifically, embodiments of the present invention utilize active discharge techniques to reduce the time constant of a resistor/capacitor (RC) circuit associated with deploying neurostimulation electrodes in a human body. Because the resistance of the living tissue is typically quite large and the capacitor used to deliver stimulation pulses of desired magnitudes while blocking direct current (DC) are also typically relatively large, the RC time constant can limit the frequency at which stimulation pulses may be delivered (such as to 250 Hz) and/or result in stimulation pulse wave forms which are other than optimal (e.g., not substantially a square pulse). Accordingly, rather than allowing a DC blocking capacitor to drain into the tissue surrounding the electrode, embodiments of the present invention follow a stimulation pulse by driving the circuit in the opposite direction to actively discharge the DC blocking capacitor, thereby reducing the circuits effective time constant.

According to embodiments of the invention, active discharge of electrode energizing pulses may be implemented selectively. For example, active discharge may be implemented when the frequency of energizing pulses exceeds a threshold, such as 200 Hz as may be associated with multi-stimulation programs. Additionally or alternatively, different active discharge modes may be selectively implemented. For example, a first mode (e.g., 1 to 4 energizing pulse to discharge driving pulse) may be implemented with respect to a first frequency range, such as 200 Hz to 500 Hz, and a second mode (e.g., 1 to 2 energizing pulse to discharge driving pulse) may be implemented with respect to a second frequency range, such as 500 Hz to 1000 Hz.

In providing active discharge according to embodiments of the invention, constant current electrode stimulation energization pulses are utilized along with corresponding constant currents driven in opposite direction. Moreover, constant current stimulation is utilized to provide additional or alternative advantages according to embodiments of the invention. For example, using constant current electrode stimulation according to embodiments, even if the impedance associated with one or more electrode changes over time, the stimulation therapy experienced by the patient will remain unchanged because it is the current between the electrodes, the current density, that triggers the therapeutic nerve response.

Embodiments of the present invention which implement constant current electrode stimulation employ a maximum voltage override. For example, in order to prevent accelerated battery drain and a risk of over stimulation in a situation where constant current is used to stimulate a plurality of electrodes, one of which has failed such that no current is delivered thereby, a maximum voltage override may be relied upon to prevent excessive voltage from being delivered to the remaining electrodes. According to embodiments, the maximum voltage override may be set with some headroom (e.g., 10%) above the voltage expected to be experienced when delivering the prescribed constant current to facilitate the aforementioned changes in impedance which are likely to occur during treatment.

Trial stimulators configured according to embodiments of the invention include a broken circuit detection feature to recognize when an electrode is not receiving a stimulation pulse. A broken circuit detection circuit of a preferred embodiment provides an alarm or other alert to a user to provide notification of the broken circuit and/or stops delivering stimulation pulses, such as to avoid a patient or clinician increasing pulse magnitude before realizing a lead has become disconnected and thereby over stimulating the patient when the lead is subsequently reconnected. The aforementioned maximum voltage override of embodiments of the invention may be utilized in providing a broken circuit detection feature. For example, when a maximum voltage override threshold for a particular channel is reached, a trial stimulator operating program may conclude that a circuit has been broken with respect to that channel.

Embodiments of the present invention provide one or more holsters for use in carrying and/or protecting a trial stimulator. According to one embodiment, a protective holster is provided for patient use to hold the trial stimulator and facilitate the trial stimulator being attached to a patient's article of clothing, such as through use of a clip on the holster. A protective holster is also preferably provided for clinician use to hold the trial stimulator and facilitate the trial stimulator being coupled to an external interface platform. Each such holster preferably is adapted to allow access to inputs, outputs, interfaces, etcetera appropriate to use by the corresponding user (e.g., patient or clinician).

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWING

For a more complete understanding of the present invention, reference is now made to the following descriptions taken in conjunction with the accompanying drawing, in which.

DETAILED DESCRIPTION OF THE INVENTION

Figure 1:
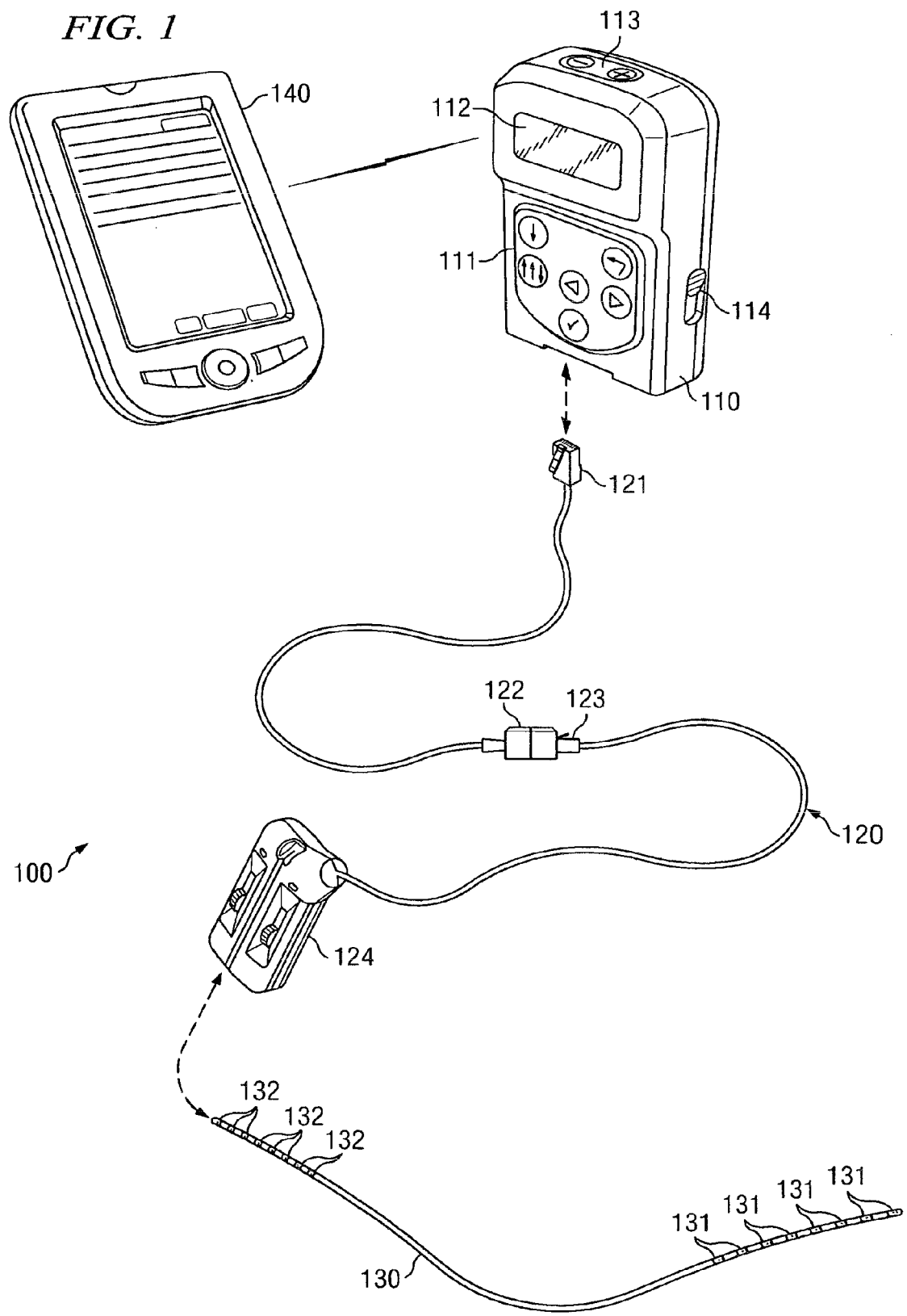
FIG. 1 shows a trial stimulator system configured according to an embodiment of the present invention.

Directing attention to FIG. 1, trial stimulator system 100 configured according to a preferred embodiment is shown. Trial stimulator system 100 is adapted to provide delivery of electronic stimulation to a patient, such as for neurostimulation, during a trial period, such as to determine if the patient is responsive to electronic stimulation therapy, to determine the parameters of a particular therapy to be implemented, etcetera. Accordingly, trial stimulator system 100 (or portions thereof) is preferably adapted for use in a plurality of situations, such as interoperatively and during patient trial. Moreover, trial stimulator system 100 (or portions thereof) is preferably adapted for use in providing stimulation to a plurality of tissues and/or areas of the body, such as spinal cord stimulation, deep brain stimulation, etcetera.

Trial stimulator system 100 of the illustrated embodiment includes trial stimulator 110, lead cable assembly 120, lead 130, and external interface platform 140. Although not shown in FIG. 1 for simplicity, trial stimulator system 100 may include one or more trial stimulator holsters for holding and/or protecting trial stimulator 110, as will be discussed in further detail below.

To facilitate user control thereof, trial stimulator 110 of the illustrated embodiment includes a user interface having keypads 111 and 113, display 112, and audio (not shown) which may include a speaker for audio output and/or a microphone for audio input. The user interface of trial stimulator 110 preferably provides a plurality of user interface modes which appears and functions substantially the same as a user interface of a pulse generator controller which will be used for controlling a pulse generator after the trial period. For example, a first user interface of trial stimulator 110 may provide a spinal cord stimulation (SCS) patient interface which appears and functions substantially the same as a patient user interface of an implanted pulse generator (IPG) controller. A second user interface of trial stimulator 110 may provide a SCS clinician interface which appears and functions substantially the same as a clinician user interface of an IPG controller. A third user interface of trial stimulator 110 may provide a deep brain stimulation patient interface which appears and functions substantially the same as a patient user interface of an IPG controller while a fourth user interface of trial stimulator 110 provides a deep brain stimulation clinician interface which appears and functions substantially the same as a clinician interface of an IPG controller.

Trial stimulator 110 couples to one or more lead cable assemblies 120, which in turn couple to one or more leads 130, to provide electronic stimulation pulses to electrodes 131. Lead 130 is inserted into a patient and positioned such that the end including electrodes 131 is disposed near nerves or other tissue (e.g., muscle) for which electronic stimulation is desired. Lead 130 may comprise a trial lead (e.g., a lead which is not for permanent use, such as may be limited to use during a trial period of 30 days) or a permanent lead (e.g., a lead that is to remain implanted after conclusion of a trial period using trial stimulator 110. Where a permanent lead is used, an extension (not shown) may be coupled to the lead to externalize the lead and to provide a suitable interface to lead cable assembly 120.

The end of lead 130 including connectors 132 is inserted into quick connect receiver 124 of lead cable 120 of the illustrated embodiment for electrical connection of electrodes 131 to appropriate signal lines of lead cable 120. Lead cable 120 of the illustrated embodiment may be coupled to trial stimulator 110 at either of connectors 121 or 123. For example, connector 121 may be coupled to trial stimulator 110, with connector 123 coupled to connector 122, to provide an extended lead cable as may be useful for clinician operation of trial stimulator 110 during implantation of lead 130. However, connector 122 may be coupled to trial stimulator 110, with the portion of lead connector 130 including connectors 121 and 122 removed, to provide a shortened lead cable as may be useful for patient trial operation of trial stimulator 110.

Lead cable connectors, such as connectors 121 and 123, utilized according to embodiments are preferably comprised of connector configurations which securely lock into trial stimulator 110, and the operation of which is readily understood by users thereof. For example, the illustrated embodiment employs a modular connector configuration corresponding to that of an RJ45 8 pin connector, which are in wide spread use for digital telephones and computer networks. The RJ45 connector configuration includes a locking tab which provides appreciable locking capabilities as well as presenting a form factor which is familiar to a great number of users. Moreover, connectors produced according to an RJ45 connector configuration may be mass produced relatively inexpensively. However, although adopting an RJ45 connector configuration, or other familiar form factor, preferred embodiments of the present invention do not utilize a connector which is directly interchangeable with a connector used for other, non-medical, systems. For example, an RJ45 connector configuration of embodiments may include a key protrusion and/or detent in a surface thereof to prevent the lead cable from being inserted into an inappropriate interface, such as a computer network interface, and/or to prevent an inappropriate cable, such as a computer network cable, from being inserted into the trial stimulator.

Figure 2:
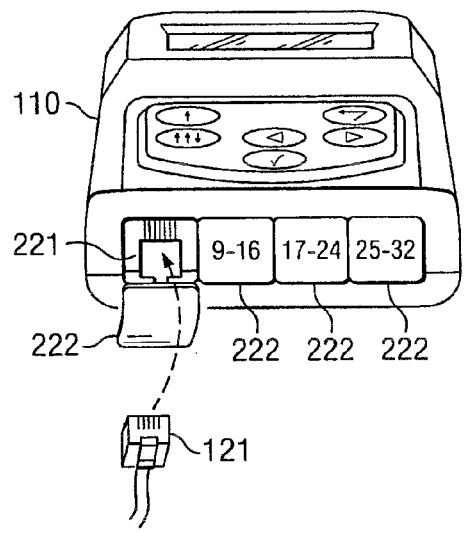
FIG. 2 shows additional detail with respect to a trial stimulator of FIG. 1.

Trial stimulator 110 of the illustrated embodiment includes a plurality of multi-channel interfaces for coupling to one or more leads as shown in FIG. 2. Specifically, the illustrated embodiment includes multi-channel interface 221 (shown in FIG. 2) as well as 3 additional multi-channel interfaces (not visible behind respective ones of flaps 222). The multi-channel interfaces provide connectivity of multiple stimulation channels (e.g., channels 1-8, channels 9-16, channels 17-24, and channels 25-32 respectively) external to trial stimulator 110, such as by mating with connector 121 of lead cable 120. When not in use, a multi-channel interface, such as multi-channel interface 221 may be covered by a corresponding one of flaps 222 for protection.

Figure 3:
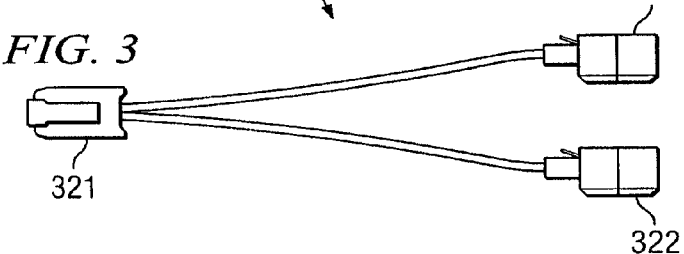
FIG. 3 shows an alternative embodiment of a lead cable assembly according to an embodiment of the invention.

It should be appreciated that, although the illustrated embodiment of trial stimulator 110 includes multi-channel interfaces accommodating 8 channels and leads having 8 electrodes, embodiments of the invention may provide for any number of channels and electrodes. Likewise, there is no limitation with respect to the use of 4 multi-channel interfaces or providing 32 independent stimulation channels according to the present invention. For example, referring to FIG. 3, lead cable "Y" adapter 320 is shown which facilitates coupling multiple leads, such as 2 leads having 4 electrodes each, to a single multi-channel interface, such a multi-channel interface 221. Embodiments of the invention may utilize leads having fewer electrodes than the number of channels supported by a trial stimulator interface to which they are connected. For example, trial stimulator 110 may detect (or a clinician may indicate) that a 4 electrode lead has been inserted into one or more of the multi-channel interfaces, such as multi-channel interface 221.

Figure 4:
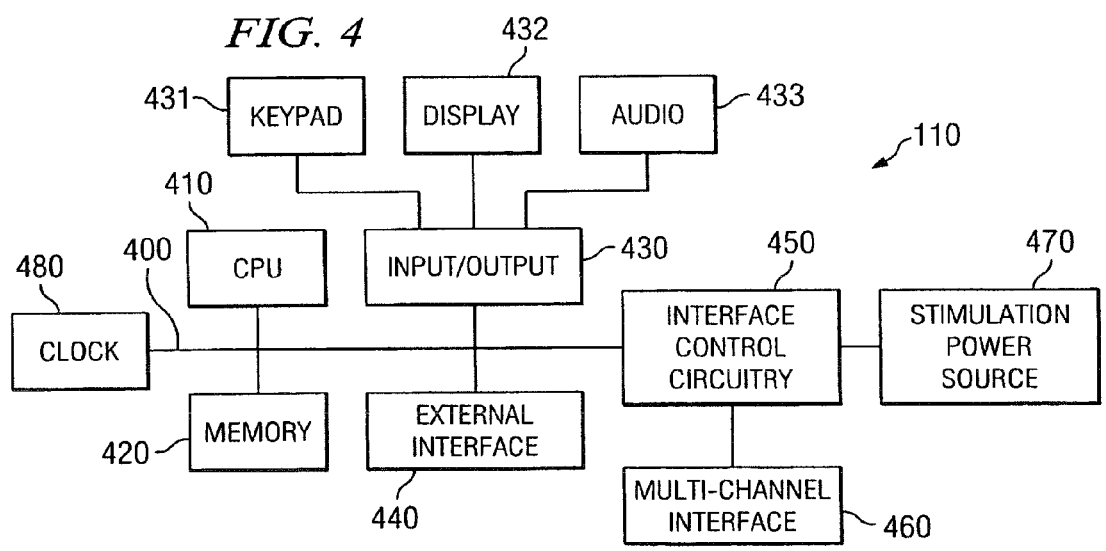
FIG. 4 shows a high level block diagram of a trial stimulator configured according to an embodiment of the present invention.

FIG. 4 provides a high level functional block diagram of trial stimulator 110 according to an embodiment of the present invention. Trial stimulator 110 of FIG. 4 includes central processing unit (CPU) 410, memory 420, input/output controller 430, external interface 440, interface control circuitry 450, and clock 480, all coupled by bus 400. Additionally, trial stimulator 110 of FIG. 4 includes multi-channel interface 460 and stimulation power source 470 coupled through interface control circuitry 450. Accordingly, trial stimulator 110 of a preferred embodiment provides an integrated pulse generator and stimulation pulse control system.

CPU 410 preferably operates under control of an instruction set and algorithms, as may be stored in memory 420, defining operation as described herein. In addition to storing the foregoing instruction set and algorithms, memory 420 may store operational data, such as stimulation parameters, stimulation programs, compliance monitor information, patient information, clinician information, historical information, user help information, and/or the like.

Input/output controller 430 of the illustrated embodiment is coupled to keypad 431, such as may correspond to keypads 111 and 113 of FIG. 1, display 432, such as may correspond to display 112 of FIG. 1, and audio 433, such as may comprise an audio speaker and/or microphone, to facilitate user control and interaction with trial stimulator 110. Accordingly, trial stimulator 110 may receive user input, such as through manipulation of keys of keypad 431 and/or by aural input through audio 433. Likewise, trial stimulator 110 may provide output to a user, such as by textual and graphical presentation on display 432 and/or by aural output through audio 433.

Display 432 is preferably configured to provide a relatively large display area. According to a preferred embodiment, display 432 comprises a 4 line by 20 character dot matrix liquid crystal display suitable for displaying text characters as well as bit mapped graphics. Display 432 may be adapted to provide gray scale display, such as 4 or 8 bit gray scale, and/or may provide color display, such as 16 bit color, and preferably includes a back light for easy viewing in many light conditions.

External interface 440, such as may correspond to interface 114 of FIG. 1, provides an external data connection for communication with devices external to trial stimulator 110. For example, external interface 440 may provide a bi-directional data link for interfacing an external clinician user interface platform, such as may be provided by external interface platform 140 of FIG. 1.

External interface 440 may provide a wireline interface, such as may comprise a serial interface (e.g., USB), a parallel interface, a local area network (LAN) interface (e.g., Ethernet), a fiber optic interface, and/or the like. Additionally or alternatively, external interface 440 may provide a wireless interface, such as may comprise a bluetooth interface, an IEEE 802.11 interface, an IEEE 802.16 interface, a cellular interface, a personal communications system (PCS) interface, an infrared interface, and/or the like. Accordingly, external interface 440 of embodiments of the present invention may provide for near field, far field, and/or long distant remote interfacing with trial stimulator 110, such as to provide control, polling, programming, status monitoring, etcetera. It should be appreciated, therefore, that external interface 440 of embodiments may provide connectivity to external devices in addition to or in the alternative to the aforementioned external interface platform. For example, external interface 440 may be utilized to provide connectivity to an external cathode ray tube (CRT), LCD flat panel display, or other display device to accommodate larger or improved display of user output. Similarly, external interface 440 may be utilized to provide connectivity to an external keyboard, digitizing tablet, digital pointer (e.g., mouse), or other input device to accommodate larger or more complex user input. Likewise, external interface 440 may be coupled to a communication device, such as a modem, network interface card (NIC), and/or wireless access point, in order to facilitate desired connectability with respect to trial stimulator 110.

Additionally or alternatively, external interface 440 may comprise an access port for reprogramming trial stimulator 110. For example, in addition to providing an interface to an external platform such as external interface platform 140 of FIG. 1, external interface 440 may comprise a hidden access port providing a proprietary interface for facilitating software upgrades, low level diagnostics, core dumps, debugging, etcetera. According to one embodiment, external interface 440 provides an access port from which instruction sets and algorithms of memory 420 may be reflashed.

Interface control circuitry 450 operates under control of CPU 410 to provide stimulation pulses from stimulation power source 470 to selected channels of multi-channel interface 460, such as may comprise one or more interfaces such as multi-channel interface 221 of FIG. 2. For example, stimulation power source 470 of a preferred embodiment may comprise a battery and circuitry to function as a constant current source which may be selectively coupled to one or more independent stimulation channels of multi-channel interface 460 by interface control circuitry 450 to provide stimulation pulses of desired magnitude, frequency, pulse width, etcetera. Similarly, stimulation power source 470 may be selectively coupled to stimulation channels of multi-channel interface 460 by interface control circuitry 450 to provide an active discharge pulse following a corresponding stimulation pulse.

Stimulation power source 470 preferably utilizes a commercially available battery, such as a 9 volt alkaline battery as is widely available through retail outlets. Accordingly, a user of trial stimulator 110 may readily replace the battery of stimulation power source 470 as needed. Additionally or alternatively stimulation power source 470 may utilize a rechargeable battery to facilitate recharging of the battery without replacement. However, such a rechargeable battery configuration, without a replaceable battery, may necessitate careful operation of trial stimulator 110 to avoid depleting the battery during a time or location that recharging is not practicable.

The battery of stimulation power source 470 provides energy for operation of circuitry of trial stimulator 110 in addition to interface control circuitry 450 according to a preferred embodiment. For example, the aforementioned battery may provide power for operation of CPU 410, memory 420, input/output controller 430, external interface 440 and/or clock 480. Accordingly, backup power circuitry, such as may comprise a capacitor or rechargeable cell, may be provided to maintain energy to select circuits for a minimum amount of time to facilitate a battery change or recharge period. For example, backup power circuitry may be provided with respect to memory 420 so that stimulation programs, stimulation parameter sets, historical information, etcetera is retained during a battery change, thereby providing a substantially non-volatile memory configuration.

Clock 480 preferably provides date and/or time information useful in the operation of trial stimulator 110. For example, clock 480 may provide a clock by which the frequency of stimulation pulses provided by interface control circuitry 450 is controlled. Additionally or alternatively, clock 480 may provide real time information, such as a time of day and/or a day of the week, for use in implementing different stimulation programs, creating a historical database, monitoring compliance, instigating communications, etcetera.

As described above, stimulation power source 470 of a preferred embodiment provides a constant current source which may be selectively coupled to one or more independent stimulation channels of multi-channel interface 460 by interface control circuitry 450 to provide stimulation pulses of desired magnitude, frequency, pulse width, etcetera. Accordingly, trial stimulator 110 of a preferred embodiment operates to provide constant current stimulation pulses. For example, interface control circuitry 450 may switchably couple a properly configured current source circuit of stimulation power source 470 to an appropriate channel of multi-channel interface 460 according to clock 480 and thereby provide constant current stimulation pulses having a desired frequency.

It should be appreciated that, if electrode impedances are identical, it does not matter whether a constant voltage pulse or a current pulse is provided in achieving a desired level of stimulation. However, if the electrode impedance changes over time, such as due to scar tissue forming around the electrodes, the lead shifting slightly due to patient movement, etcetera, constant current stimulation is preferred over constant voltage stimulation because it is the current between the electrodes (the current density) that triggers the nerve to deliver therapeutic responses in neurostimulation. Accordingly, using a constant current stimulation pulse according to embodiments of the present invention, a constant current field is provided around the electrodes, irrespective of what the impedance change is, thereby consistently delivering the desired stimulation response.

It might be argued that use of a constant current source in providing the foregoing stimulation runs a risk of depleting the battery faster and/or over stimulation (e.g., voltages appreciably in excess of those associated with desired/prescribed currents with the expected impedance/load) in a situation where one or more electrodes become unexpectedly disconnected from the constant current source. For example, where a constant current source is configured to provide a desired current to 2 electrodes and 1 of those electrodes becomes disconnected (the impedance experienced by the system changes), the remaining electrode may be provided with a voltage twice that desired. However, it should be appreciated that the constant voltage configurations of prior art stimulators run a risk of over stimulation due to both voltage and current being a part of Ohm's Law. In particular, if a constant voltage stimulator loses an electrode due to it becoming short circuited (i.e., substantially zero voltage across the electrode), the impedance of the system would change resulting in an increased current being delivered to electrodes and correspondingly an over stimulation situation (whereas, in a constant current system, the current would remain the same).

To address the foregoing risk of depleting the battery faster and/or over stimulation, preferred embodiments of interface control circuitry 450 implement a constant current which is voltage limited. For example, CPU 410 may operate to determine an appropriate voltage limit (e.g., maximum override voltage threshold) to establish with respect to a constant current pulse which may be utilized by interface control circuitry 450 to allow provision of a desired current while preventing an over stimulation situation by establishing a maximum voltage for the stimulation pulse. By knowing the impedance or voltage at a current setting associated with an electrode, CPU 410 may select a voltage limit which allows some amount of voltage (e.g., a percentage, such as 10%) in excess of that associated with delivering a prescribed current to the tissue to be stimulated while providing adequate over stimulation protection. Such voltage limits are preferably determined automatically, such as upon a stimulation current level being selected or adjusted (e.g., a stimulation parameter set being adjusted), and may be established with respect to every stimulation pulse (including the pulses of a multi-stimulation program). This voltage limit information may be provided by CPU 410 to interface control circuitry 450 for use in controlling signals to multi-channel interface 460.

Voltage limits for use with respect to each stimulation parameter set may be determined according to embodiments using a voltage ramping technique. For example, when a stimulation parameter set is selected or adjusted, embodiments of the invention may operate to increase voltage limit in small increments, making a compliance check to see if the voltage is high enough to deliver the desired or prescribed constant current pulse. If the desired or prescribed constant current pulse is not delivered with a particular value of voltage limit, the voltage limit may again be increased until a current compliance check error is eliminated. The voltage limit at that point (or perhaps some slightly increased value as discussed above) may be recorded for use with respect to the stimulation parameter set and the process repeated for each of the stimulation parameter sets within a multi-stimulation program. Therefore, a constant current system of embodiments of the present invention implementing a voltage limit will not over stimulate the patient or deplete the battery more quickly. In contrast, the prior constant voltage systems may over stimulate the patient and continuous current systems without a voltage limit may deplete the battery more quickly.

Additionally or alternatively, impedance testing is provided by the circuitry of trial stimulator 110 of preferred embodiments. For example, impedance testing may be utilized according to embodiments of the invention in determining electrode impedances (e.g., determining the load to be driven by a constant current source), such as for use in automatically establishing the foregoing voltage limits. Likewise, impedance testing may be utilized in providing a broken circuit detector (e.g., as may be implemented periodically, before each stimulation pulse, before particular stimulation pulses, etcetera), such as for use in alerting a patient or clinician that an electrode or electrodes are not coupled to the trial stimulator and therefore stimulation pulses are not being delivered thereto. A broken circuit detection circuit of a preferred embodiment provides an alarm or other alert to a user to provide notification of the broken circuit and/or stops delivering stimulation pulses, such as to avoid a patient or clinician increasing pulse magnitude before realizing a lead has become disconnected and thereby over stimulating the patient when the lead is subsequently reconnected. The aforementioned maximum voltage override of embodiments of the invention may be utilized in providing a broken circuit detection feature. For example, when a maximum voltage override threshold for a particular channel is reached, a trial stimulator operating program may conclude that a circuit has been broken with respect to that channel. Such a maximum voltage override threshold may be used in combination with impedance data in determining a broken circuit condition according to embodiments of the invention. Impedance data may also be used to help determine the proper location of the leads/electrodes, predict battery life, help select implanted devices, etcetera.

Although some stimulation systems in the past have implemented a light emitting diode (LED) to indicate when current was flowing to an electrode or electrodes, such configurations provide no information with respect to the impedance. Moreover, in order for the LED to be illuminated according to such configurations, an appreciable voltage level must be present, such as on the order of 1 Volt, thereby making their use in determining electrode connectivity without providing stimulation which is perceptible to a patient substantially impossible. Such voltage levels may not be present in particular situations, such as deep brain stimulation, without over stimulation, thereby making the LED configuration ineffective in such situations.

According to an embodiment, interface control circuitry 450 operates under control of CPU 410 to provide impedance test signals by coupling circuitry of stimulation power source 470 to channels of multi-channel interface 460. In measuring impedance, interface control circuitry 450 may cause low level pulses to be applied to the electrodes for which impedance testing is being performed. Preferably, the pulses are of a low magnitude, such as on the order of 50 to 100 microamps, and/or at a relatively high frequency, such as on the order of 50 kHz (e.g., 10 microsecond pulse width), so that the impedance test signals do not provide stimulation which is detected by the patient. In operation according to an embodiment, CPU 410 analyzes the voltage across the load during these impedance test signals to determine impedance.

According to a preferred embodiment, the impedance test signals are provided as an alternating current (AC), substantially square wave, wherein an electrode is an anode during a first portion of the square wave and a cathode during a second portion of the square wave. Accordingly, interface control circuitry 450 may switchably connect constant current circuitry of stimulation power source 470 to the aforementioned electrode in a forward and reverse configuration to provide high frequency impedance test signals without requiring substantial control of stimulation power source 470 to provide the aforementioned square wave. In this configuration, wherein a constant current source is utilized, it should be appreciated that the voltage across the load is proportional to the impedance. By applying the foregoing AC impedance test signal to electrodes for an appreciable time, e.g., on the order of milliseconds, the differential voltages may be averaged, perhaps using filtering, to provide impedance information. For example, the differential voltage change across the load may be converted to a direct current (DC) value and provided to an analog to digital (A/D) converter for use in determining an impedance value by CPU 410. In particular, the DC voltage will be linearly proportional to impedance according to embodiments, thereby providing information useful for determining impedance.

The foregoing impedance testing technique implemented according to preferred embodiments provides a very low pulse width and very low amplitude so that no perceptible stimulation will be delivered to a patient, including deep brain stimulation patients where the stimulation values are very low themselves. Moreover, filtering the differential voltages over a long period of time according to embodiments of the invention provides for very accurate impedance determinations, such as within a few percent, and over a very large range, such as over a range of from 100 Ohms to 5 kOhms.

It should be appreciated that in the foregoing impedance testing may be utilized to provide an impedance value associated with an electrode or electrodes. Moreover, the foregoing impedance testing may be utilized in providing a broken circuit detector or other fault detector, such as by concluding that a broken circuit is present with respect to an electrode when an impedance value is determined to be excessively high and/or concluding that a short circuit is present with respect to an electrode when an impedance value is determined to be excessively low. The foregoing information may be provided to a user, such as a patient or clinician, through output via a user interface of trial stimulator 110.

Embodiments of the present invention utilize impedance testing, such as using the techniques described above, in providing system diagnostics. For example, upon power up, and/or at other appropriate times, trial stimulator 110 may operate to provide system diagnostics to verify the operational status of aspects of system 100. Where a trial lead has been placed in a patient and a clinician is preparing to program trial stimulator 110 to provide stimulation, CPU 410 may first operate to determine that the impedances associated with each electrode is within expected ranges, and thus that the electrodes are connected properly, that the lead is disposed properly, that the patient is a suitable candidate for electrostimulation therapy, etcetera.

According to a preferred embodiment, CPU 410 controls interface control circuitry 450 to couple stimulation power source 470 to channels of multi-channel interface 460, and thus the corresponding electrodes. Specifically, electrodes may be energized in bipole pairs (cathode and anode), "walking" the test signals from bipole pair to bipole pair to obtain impedance information for each electrode and thereby test all the connections. For example, in determining system integrity a diagnostic algorithm may provide a test signal to channels 1 and 2 (corresponding to electrodes 1 and 2) wherein the electrodes are energized as bipoles (plus/minus), wherein this bipole energization is repeated for the other electrodes in bipole pairs (electrodes 2 and 3, electrodes 3 and 4, etcetera). By measuring the impedance in each such step, conclusions may be made with respect to each channel and associated electrode. For example, if an open circuit is detected with respect to channels 1 and 2 (electrodes 1 and 2), testing of channels 2 and 3 (electrodes 2 and 3) should provide information as to whether channel 1 (electrode 1) or channel 2 (electrode 2) is the source of the open circuit.

CPU 410 may provide conclusions based upon impedances associated with an electrode being within an expected range (e.g., 200-3000 Ohms), too low, or too high. For example, if an impedance associated with an electrode is not within an expected range, a user interface of trial stimulator 110 may provide a warning to the user, e.g., a clinician, and/or make suggestions with respect to correcting the problem, e.g., suggesting that the connections be checked, suggesting that the position of the lead be verified, etcetera.

Embodiments of the present invention are adapted to provide active discharge which respect to stimulation pulses in order to facilitate high pulse rate (high frequency) operation. For example, trial stimulator 110 of a preferred embodiment may be utilized to provide stimulation pulse frequencies anywhere in the range of from 2 Hz to 1200 Hz. However, the impedances associated with electrodes implanted in living tissue may be relatively high, such as on the order of 1500 Ohms. In providing stimulation to the electrodes, DC current is preferably blocked to prevent tissue damage, such as may result from electroplating. Accordingly, interface control circuitry 450 and/or multi-channel interface 460 of preferred embodiments include DC blocking capacitors with respect to each channel so that there is no net DC associated with the stimulation pulses. Accordingly, it should be appreciated that there will be a resistor/capacitor (RC) time constant associated with the stimulation circuit according to embodiments. This RC time constant may be appreciably large because the pulses may be on the order of milliamps and the resistance may be relatively large.

Figure 5A:
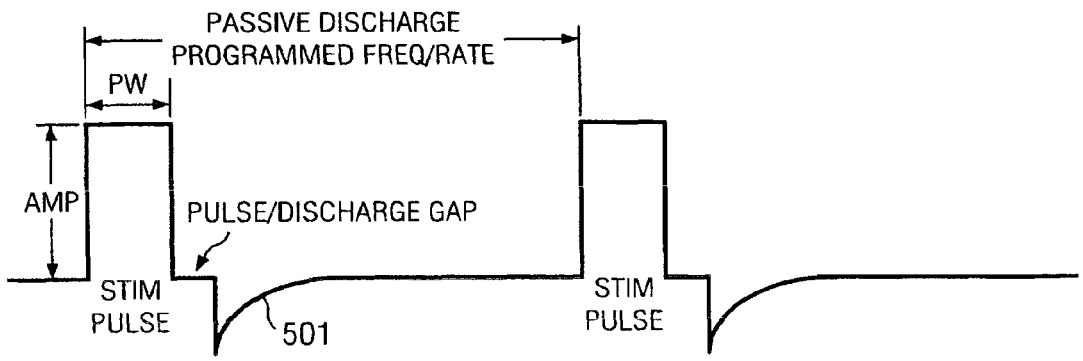
FIG. 5A shows a graph of passive discharge provided with respect to a stimulation pulse of a trial stimulator adapted according to embodiments of the present invention.

Directing attention to FIG. 5A, a graph of a stimulation signal associated with passive discharging of the foregoing RC circuit is shown. In particular, passive discharge curve 501 represents the foregoing RC time constant, which if not allowed to reach a transient state will affect the subsequent stimulation pulse shape. From FIG. 5A it can be seen that passive discharging of the RC circuit may provide acceptable results when stimulation pulses are spaced apart sufficiently in time (e.g., low frequency stimulation, such as 250 Hz or below). However, as stimulation pulses are moved closer and closer together in time, passive discharge curve 501 will not be allowed to return to a transient state and, thus, subsequent stimulation pulses will be affected.

Embodiments of trial stimulator 110 provide for high frequency stimulation pulses. In particular, trial stimulator 110 of a preferred embodiment provides for multi-stimulation programs wherein stimulation parameter sets of multiple stimulation programs are interleaved on a pulse-by-pulse basis. Even where a particular stimulation program provides for stimulation pulses with a frequency of 100 Hz (a relatively low frequency stimulation program), a multi-stimulation program wherein 8 such stimulation programs are interleaved on a pulse-by-pulse basis results in a stimulation pulse frequency of 800 Hz (a relatively high stimulation pulse frequency).

Figure 5B:
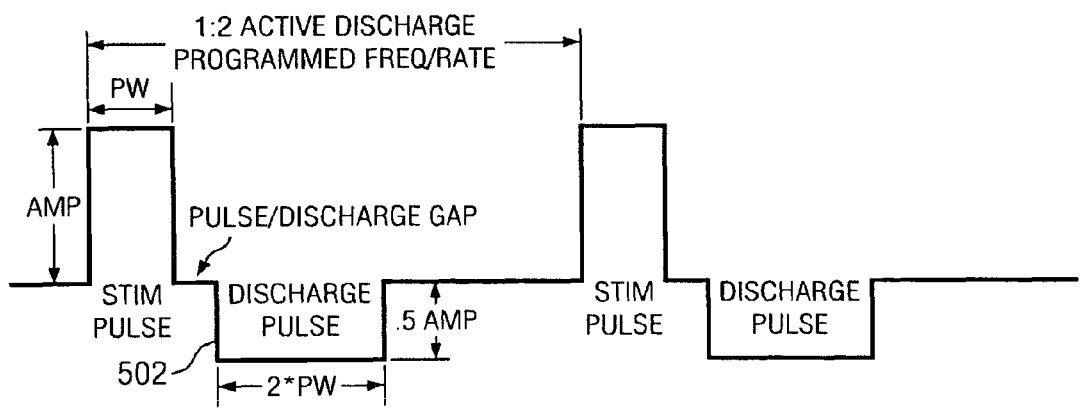
FIGS. 5B-5C show graphs of active discharge provided with respect to stimulation pulses of a trial stimulator adapted according to embodiments of the present invention.
Figure 5C:
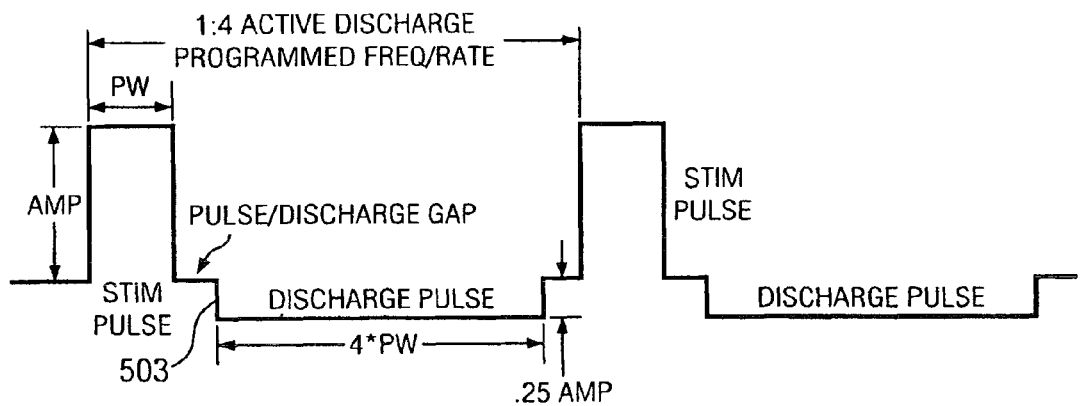

Active discharge is implemented according to embodiments of the present invention to facilitate high frequency stimulation pulses. In providing active discharge according to embodiments, interface control circuitry 450 couples stimulation power source 470 to channels of multi-channel interface 460 such that current is driven in a first direction for a period of time, thereby providing a stimulation pulse, and then driven in a second, or reverse, direction for a period of time, thereby providing a discharge pulse. FIGS. 5B and 5C show graphs of stimulation signals associated with active discharging of the foregoing RC circuit. In particular, active discharge pulses 502 and 503 (of FIGS. 5B and 5C respectively) actively discharge the RC circuit, facilitating placing stimulation pulses closer together in time.

In order to provide complete discharge of the RC circuit, the energy of the discharge pulse (the area of the discharge pulse curves as shown in FIGS. 5B and 5C) is preferably equal to the energy of the proceeding stimulation pulse (the area of the stimulation pulse curves as shown in FIGS. 5B and 5C). However, as can be seen by discharge pulses 502 and 503, the pulse width and amplitude of the discharge pulses need not be the same as the pulse width and amplitude of the stimulation pulse. It should be appreciated that constant current stimulation implemented according to embodiments of the present invention simplifies implementation of active discharge as described above due to the pulse amplitudes (current) being known and constant.

According to a preferred embodiment, the amplitude of a discharge pulse is substantially minimized in order to avoid its being perceived by the patient, or otherwise impacting the therapeutic effects of the stimulation pulse. Accordingly, where stimulation pulse frequency is lower, the pulse width of the discharge pulse may be lengthened (and correspondingly the amplitude of the discharge pulse may be decreased) as shown in FIG. 5C. However, as stimulation pulse frequency is increased, the pulse width of the discharge pulse may be shortened (and correspondingly the amplitude of the discharge pulse may be increased) as shown in FIG. 5B to facilitate stimulation pulses more closely spaced in time.

The foregoing active discharge is implemented selectively, according to embodiments of the invention. For example, CPU 410 may operate to implement active discharge when the frequency of energizing pulses exceeds a threshold, such as 200 Hz. Accordingly, where a stimulation program or multi-stimulation program provides stimulation pulses at a frequency of 200 Hz or below, passive discharge as shown in FIG. 5A may be used. CPU 410 of the illustrated embodiment may selectively implement different active discharge modes. For example, a 1 to 4 energizing pulse to discharge driving pulse mode as illustrated in FIG. 5C may be implemented with respect to a first frequency range, such as 200 Hz to 500 Hz, and a 1 to 2 energizing pulse to discharge driving pulse mode as illustrated in FIG. 5B may be implemented with respect to a second frequency range, such as 500 Hz to 1000 Hz.

External interface platform 140, as may be used to interface with and/or control trial stimulator 110, may comprise any number of processor-based systems which provide suitable input/output for providing a user interface as described herein and for interfacing with trial stimulator 110. For example, external interface platform 140 of embodiments of the present invention comprise a personal digital assistant (PDA), such as a pocket PC operable under control of the WINDOWS CE operating system, as are well known in the art. A PDA may provide a particularly desirable external interface platform because of their portability, their wide availability, their relatively versatile display and user input characteristics, their ability to be interfaced using a variety of media (whether wireless or wireline) and protocols, and their ability to be configured to provide dedicated operation (i.e., to the exclusion of other application programs) as an external interface according to the present invention. Accordingly, external interface platform 140 comprises a PDA operable under control of an instruction set defining operation as described herein, according to embodiments of the present invention. Of course, external interface platform 140 may comprise a processor-based system other than the aforementioned PDA. For example, external interface platform 140 of embodiments of the present invention comprises a general purpose portable computer system, such as a notebook computer operable under control of a WINDOWS, LINUX, MAC OS, UNIX, or operating system, and having an instruction set defining operation as described herein. According to alternative embodiments of the invention, external interface platform 140 comprises a special purpose device, such as may include application specific integrated circuits (ASICs), firmware, etcetera, adapted to provide operation as described herein.

Having described trial stimulator 110, lead cable assembly 120, lead 130, and external interface platform 140, of embodiments of the present invention, operation of trial stimulator system 100 in providing trial stimulation according to embodiments of the invention shall be described. Trial stimulator system 100 of embodiments of the present invention may be used in providing stimulation to a plurality of tissues and/or areas of the body, such as spinal cord stimulation, deep brain stimulation, peripheral nerve stimulation, vagas nerve stimulation, gastric stimulation, occipital nerve stimulation, sacral root nerve stimulation, etcetera. Accordingly, a user interface provided by trial stimulator 110 and/or external interface platform 140 provides multi-mode patient and/or clinician interfaces adapted to present an interface specific to a particular use. For example, although perhaps sharing a number of features and functions, separate patient and/or clinician interfaces for spinal cord stimulation and deep brain stimulation may be provided with respect to trial stimulator 110 and external interface platform 140. Utilization of a particular mode may provide for different trial stimulator operating characteristics, such as to implement smaller or larger amplitude increments when adjusting a stimulation pulse amplitude parameter in the various modes of operation.

Trial stimulator system 100 is adapted for use in a plurality of situations, including interoperative use and patient trial use. Accordingly, trial stimulator 110 of a preferred embodiment provides a user interface which is adapted for patient trial use. For example, trial stimulator 110 may provide an intuitive interface having graphical, textual, and/or aural prompting and simple user input. According to one embodiment, graphical displays such as may include a battery life indicator, stimulation pulse amplitude and/or frequency, etcetera are provided to aid a user in readily interpreting the status of various aspects of a trial stimulator. Trial stimulator 110 of a preferred embodiment provides a patient interface which appears and functions substantially the same as a user interface of a pulse generator controller which will be used for controlling a pulse generator (implanted or otherwise) after the trial period, thereby allowing a patient to learn a single interface.

Embodiments of trial stimulator 110 additionally or alternatively provide a user interface which is adapted for clinician use. For example, a trial stimulator user interface configured according to embodiments of the invention may facilitate simplified use between a plurality of patients by automatically resetting stimulation parameter sets and/or other parameters to an initialization state (or perhaps querying a clinician in this regard) when a clinician mode is entered. A clinician user interface of trial stimulator 110 may provide additional features, such as a compliance monitor, system diagnostic options, etcetera. For example, a compliance monitor may record information with respect to the operation of a trial stimulator, including stimulation parameters, programs implemented, time and duration of operation of stimulation sets, etcetera, in order to allow a clinician to subsequently determine if a patient has used the trial stimulator according to a prescribed therapy, to diagnose a patient's reported indications, etcetera. Diagnostic options may facilitate a clinician verifying proper operation of various aspects of a trial stimulator, such as to implement the above described impedance testing techniques. Although such diagnostics may be implemented automatically, such as on power up or upon entering a programming mode, the clinician user interface may provide the results of such diagnostics to the user. Moreover, such diagnostic routines may be implemented under control of a user, via the aforementioned user interface, such as to facilitate testing of a lead and its electrodes when a pulse generator is being replaced at the end of its battery life. Such diagnostics may allow a clinician to avoid the unnecessary replacement of a lead during the procedure.

Full clinician user interface functionality, such as may include initialization, programming, monitoring, status reporting, etcetera, is preferably included within trial stimulator 110. For example, a clinician interface incorporated within trial stimulator 110 of an embodiment may provide an interface which appears and functions substantially the same as a clinician interface of a pulse generator controller which will be used for controlling a pulse generator (implanted or otherwise) after the trial period, thereby allowing a clinician to learn a single interface.

In use, a clinician may insert lead 130 into a patient for which neurostimulation trial using trial stimulator 110 is desired. Lead 130 may be coupled to trial stimulator 110 via lead cable assembly 120. According to embodiments of the invention, trial stimulator 110 may remain outside of a sterile field associated with the patient by employing an extension cable portion of lead cable assembly which ends at connector 122 and connector 121. In particular, lead cable assembly 120 having the aforementioned extension cable portion included therewith provides a lead cable which is relatively long, such as on the order of 6 feet, to facilitate its being run beyond the drapes of a surgical sterile field.

Once coupled to lead 130, a clinician may utilize keypads 111 and 113, display 112, and/or audio (not shown) of trial stimulator 110 to perform various functions, such as power up, diagnostics, patient initialization, stimulation parameter set programming, multi-stimulation programming, etcetera. Of course, one or more of the foregoing may be performed without trial stimulator 110 being coupled to lead 130, if desired.

In operation according to a preferred embodiment, upon power up of trial stimulator 110 and/or when coupled to lead 130, when entering a clinician mode, diagnostic routines are preferably entered to provide impedance testing of the channels and associated electrodes. Accordingly, connection information, and perhaps alarms, may be provided to a clinician or other user. Such information is particularly useful in providing programming of trial stimulator 110 because a connection between trial stimulator 110 and one or more of electrodes 131 may be missed, such as by misalignment of contacts 132 in quick connect assembly 124, resulting in a clinician believing that a patient is being stimulated when in fact the patent is not. With the foregoing impedance check, it can be confirmed that the stimulation pulses are in fact making it into the patient's body. Additionally or alternatively, the foregoing impedance information may be utilized to determine if the patient is a good candidate for electrostimulation, such as where the electrodes are disposed in a particularly high impedance spot making the patient poorly suited for electrostimulation using an implantable generator (although perhaps a RF generator having a larger battery capacity may still provide suitable operation).

Additionally or alternatively, entry of a clinician mode trial stimulator 110 queries the clinician as to whether a new patient is trialing the stimulator so as to facilitate simplified resetting parameters as well as to ensure that a previous patient's stimulation programs are not accidentally implemented with respect to a subsequent patient.

In clinician mode, a clinician may set/adjust the parameters of a stimulation program or programs. For example, a clinician may set amplitude, pulse width, frequency, and electrodes to create one or more stimulation parameter sets of a stimulation program or multi-stimulation program.

A clinician interface of trial stimulator 110 may provide for selection of amplitude with respect to any electrode through programming a constant current source. According to a preferred embodiment, multiple ranges of amplitude are selectable, each of which provides multiple bits of amplitude resolution. For example, three amplitude ranges, such as from 0 to 6.125 milliamps, from 0 to 12.25 milliamps, and from 0 to 25.5 milliamps. According to an embodiment, each amplitude provides 256 bits of resolution. Accordingly, the 6.125 milliamp range provides for increments of 0.025 milliamps, the 12.25 milliamp range provides for increments of 0.05 milliamps, and the 25.5 milliamp range provides for increments of 0.1 milliamps. Selection of the appropriate amplitude range and step size may be made by selecting the indication the trial stimulator is being used for. For example, selecting "deep brain stimulation" may select the 0 to 12.25 milliamp range and provide for 0.05 milliamp adjustment increment steps, while selecting "spinal cord stimulation" may select the 0 to 25.5 milliamp range and provide for 0.1 milliamp adjustment increment steps.

Pulse width with respect to any electrode as selectable through a clinician interface of trial stimulator 110 of an embodiment may provide a range of pulse widths from 20 microseconds to 500 microseconds, although alternative embodiments provide for pulse widths in the range of 10 microseconds to 1000 microseconds. The ranges of pulse widths made available according to embodiments of the invention may be adjusted based upon the particular type of stimulation being implemented, e.g., spinal cord stimulation, deep brain stimulation, etcetera. Trial stimulator 110 of an embodiment provides pulse width selection resolution of 10 microsecond, although other pulse width resolutions may be implemented according to the concepts of the invention.

Frequency with respect to any electrode as selectable through a clinician interface of trial stimulator 110 of an embodiment may provide a range of frequencies from 2 to 1200 Hz. According to embodiments of the invention, frequency selection step sizes provided by a clinician interface are adjusted to correspond to a frequency range of the stimulation pulse. For example, when a stimulation pulse frequency is low, frequency selection step sizes may be small, e.g., 2 Hz, whereas when a stimulation pulse frequency is higher, frequency selection step sizes may be larger, e.g., 10 Hz, and so on. According to a preferred embodiment, frequency step sizes go from 2 to 250 Hz in 2 Hz steps, from 250 to 500 Hz in 5 Hz steps, and from 500 to 1200 Hz in 10 Hz steps.

Embodiments of trial stimulator 110 implement active discharge as described above when stimulation pulse frequencies exceed a threshold. For example, when a stimulation frequency, whether associated with a single stimulation program or a multi-stimulation program, exceeds 250 Hz, active discharge is implemented.

The foregoing clinician functions, as well as additional clinician functions well known in the art, are preferably provided by a clinician interface of trial stimulator 110 in a format corresponding to a clinician interface of a pulse generator expected to be used long term by the patient. Accordingly, a clinician may be enabled to use the foregoing interface without substantial or additional training. However, in order to facilitate an intuitive patient interface and full featured and intuitive clinician interface without presenting a number of inputs and/or outputs which, although present in a patient trial mode, are not used by a patient, embodiments of the present invention implement an external clinician interface as provided by external interface platform 140.

According to embodiments of the invention, external interface platform 140 couples to trial stimulator 110 and allows the clinician to take control of trial stimulator 110 using external interface platform 140. Accordingly, although a clinician may be enabled to access all features and functions through manipulation of an interface integral with trial stimulator 110, a more robust interface, perhaps using enhanced graphics, color, sound, speech recognition, etcetera, may be provided to a clinician using external interface platform 140.

External interface platform 140 of a preferred embodiment operates under control of trial stimulation software to define operation as described herein. For example, menus may be presented to access various functions as described above with respect to a clinician interface of trial stimulator 110. However, external interface platform 140 preferably utilizes resources thereof to provide enhanced input/output. For example, in implementing the aforementioned diagnostic modes, external interface platform 140 may present the impedance ranges of each electrode in graphical form, or some other easily understood format. Moreover, additional processing may be provided by external interface platform 140, such as to place information in spreadsheets, to compile graphs, to analyze data, keep patient records, etcetera.

Additionally or alternatively, external interface platform 140 of embodiments may provide processing to supplement or replace that of trial stimulator 110 when coupled thereto. For example, the aforementioned techniques for determining impedances of electrodes may be sufficiently processor intensive to require appreciable time in completing diagnostics by trial stimulator 110. Accordingly, when coupled to external interface platform 140 the processing power of the external interface platform may be utilized to complete such diagnostic processing more rapidly.

A holster or housing is preferably provided for use by a clinician when external interface platform 140 is coupled to trial stimulator 110. For example, a piggyback holster arrangement, wherein a single holster assembly holds both trial stimulator and external interface platform 140 in a back-to-back configuration facilitates the holding together of the foregoing devices for simplified use in the operating room. Preferably, such a piggyback holster provides protection of trial stimulator 110, such as to cover one or more key pad buttons, display, interface ports, etcetera for which access is not needed during programming or clinician trial. However, interfaces such as interface 221 and 114 are preferably unobstructed by the aforementioned piggyback holster configuration to facilitate coupling of trial stimulator 110 to lead cable assembly 120 and to external interface platform 140. Additionally, a preferred embodiment of a piggyback holster provides a gap to facilitate wrapping of excess cable, e.g., excess portions of lead cable assembly 120, around the holster while trial stimulator 110 and external interface platform 140 are in use.

After having been programmed by a clinician, trial stimulator 110 is preferably made available for trial by a patient. Accordingly, where external interface platform 140 has been used in programming, external interface platform 140 is preferably uncoupled from trial stimulator 110. Likewise, the aforementioned piggyback holster may also be removed. Because the patient is unlikely to need the length of lead cable used by a clinician, an extension portion of lead cable assembly 120 may be removed such that connector 123 is directly interfaced with trial stimulator 110. Accordingly, a patient need not deal with an excessive amount of lead cable being coiled during a patient trial according to embodiments of the invention.

A holster or other housing is preferably provided to facilitate a patient's trial of the stimulator. For example, a protective holster having a clip which rotates 180 degrees may be provided to hold trial stimulator 110 on an article of clothing for patient access. The holster may provide a keypad cover to protect accidental keypad presses, preferably leaving particular keys available, such as stimulation off, increase/decrease stimulation amplitude, or other keys typically accessed in normal use.

Although the present invention and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. A stimulator system for generating electrical pulses for application to tissue of a patent, the system comprising:
 a processor for controlling the system under control of executable instructions;
 stimulation source circuitry for generating electrical pulses for application to tissue of the patient; and
 capacitors coupled between the stimulation source circuitry and outputs of the stimulator system;
 wherein the processor is programmed to control the stimulation source circuitry to provide stimulation according to a multi-stimulation set program that defines multiple pulses to be interleaved according to respective sets of pulse parameters, wherein a multi-stimulation set program defines a program pulse frequency;
 wherein the processor is further programmed to selectively apply active discharge of capacitors according to the program pulse frequency of a respective multi-stimulation set program by selecting from (i) a first mode of operation that employs an active discharge pulse amplitude that is a first fraction of a preceding stimulation pulse for a program pulse frequency above a first frequency threshold and below a second frequency threshold, and (ii) a second mode of operation that employs an active discharge pulse amplitude that is a second fraction of a preceding stimulation pulse for a program pulse frequency above the second frequency threshold, wherein the second fraction is less than the first fraction.

2. The system of claim 1 wherein the system is a trial stimulation system that is capable of emulating at least two different implantable pulse generators and provides distinct user interfaces for the at least two different implantable pulse generators.

3. The system of claim 1 wherein the processor is further programmed to monitor operation of the system for detection of use of the system by the patient in accordance with a prescribed therapy.

4. The system of claim 1 further comprising:
an impedance testing circuit operable in cooperation with said stimulation source circuitry to provide impedance information associated with electrodes coupled to said system.

5. The system of claim 1 wherein the stimulation source circuitry provides substantially constant current pulses.

6. The system of claim 5 wherein the processor is programmed to apply a voltage maximum limit for pulses of a multi-stimulation set program to prevent a constant current pulse from exceeding the voltage maximum limit.

7. The system of claim 1 wherein the processor is programmed to allow passive discharging of the capacitors for a program pulse frequency that is less than the first frequency.

* * * * *

UNITED STATES PATENT AND TRADEMARK OFFICE
CERTIFICATE OF CORRECTION

PATENT NO.         : 7,937,158 B2                                Page 1 of 1
APPLICATION NO.    : 12/243632
DATED              : May 3, 2011
INVENTOR(S)        : Erickson et al.

It is certified that error appears in the above-identified patent and that said Letters Patent is hereby corrected as shown below:

Column 22, claim 1, line 31, delete "patent" and replace with --patient--.

Signed and Sealed this
Ninth Day of August, 2011

David J. Kappos
*Director of the United States Patent and Trademark Office*